(12) United States Patent
Gordon, III et al.

(10) Patent No.: US 8,692,201 B1
(45) Date of Patent: Apr. 8, 2014

(54) MOISTURE DETECTION SYSTEM AND METHOD

(75) Inventors: Clarence Lavere Gordon, III, Renton, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 33 days.

(21) Appl. No.: 13/014,059

(22) Filed: Jan. 26, 2011

(51) Int. Cl.
  *G01J 5/02* (2006.01)

(52) U.S. Cl.
  USPC .................................................. 250/341.1

(58) Field of Classification Search
  USPC ....................... 250/338.1–338.5, 341.1–341.8
  See application file for complete search history.

(56) References Cited

U.S. PATENT DOCUMENTS

| | | | |
|---|---|---|---|
| 4,832,932 A * | 5/1989 | Tada et al. ................... | 423/447.2 |
| 6,847,448 B2 | 1/2005 | Nagashima et al. | |
| 7,852,466 B2 | 12/2010 | Itsuji | |
| 2003/0016358 A1 * | 1/2003 | Nagashima et al. ........... | 356/364 |
| 2007/0158571 A1 * | 7/2007 | Cole et al. ................... | 250/341.8 |
| 2007/0257194 A1 * | 11/2007 | Mueller ...................... | 250/341.8 |
| 2009/0231571 A1 * | 9/2009 | Itsuji ............................ | 356/51 |

FOREIGN PATENT DOCUMENTS

JP        2006105787 A *  4/2006

OTHER PUBLICATIONS

Zhang et al., "Terehertz imaging for water content measurement," 2008, Proceedings of 2008 International Symposium on Electrical Insulating Materials, Yokkaichi, Mie, Japan, pp. 87-90.*

Karpowics et al., "Compact continuous-wave subterahertz system for inspection applications," 2005, Applied Physics Letters, vol. 86, pp. 054105-1 to 054105-3.*

Nagali et al., "Design of a diode-laser sensor to monitor water vapor in high-pressure combustion gases," 1997, Applied Optics vol. 36, No. 36, pp. 9518-9527.*

Hadjiloucas et al.,"Analysis of spectroscopic measurements of leaf water content at terahertz frequencies using linear transforms," 2002, Journal of Optical Society of America, vol. 19, No. 12, pp. 2495-2509.*

Wietzke et al., "Industrial applications of THz systems,", 2009, SPIE Proceedings, vol. 7385, pp. 738506-1 to 738506-13.*

Stoik et al., "Nondestructive evaluation of aircraft composite using reflective terahertz time domain spectroscopy," 2010, NDT&E International, vol. 43, pp. 106-115.*

Albert Redo-Sanchez et al, "Damage and Defect Inspection with Terahertz Waves", The fourth international workshop and advanced methods for nondestructive testing and material characterizing, Jun. 19, 2009, published in www.ndt.net.

Karpowicz et al, "Compact continuous-wave subterahertz system for inspection applications", 2005 American Institute of Physics http://apl.org/apl/copyright.isp.

Siegel, "Terahertz Technology," IEEE Transactions on Microwave Theory and Techniques, vol. 50, No. 3, Mar. 2002, pp. 910-928.

Banerjee et al., "Diagnosing Water Content in Paper by Terahertz Radiation," Optics Express, vol. 16, Issue 12, Jun. 2008, pp. 9060-9066.

* cited by examiner

*Primary Examiner* — Kiho Kim

(74) *Attorney, Agent, or Firm* — Yee & Associates, P.C.

(57) ABSTRACT

A moisture detection system for characterizing moisture on a sample includes a generator adapted to emit an incident beam of radiation from the terahertz spectrum of frequency onto the sample; a detector adapted to receive a reflected beam of radiation from the sample and measure radiation in the reflected beam; and a controller adapted to correlate the radiation in the reflected beam with an amount of moisture on the sample.

16 Claims, 4 Drawing Sheets

MOISTURE DETECTION SYSTEM AND METHOD

TECHNICAL FIELD

The disclosure generally relates to detection of moisture on carbon fiber composite materials. More particularly, the disclosure relates to a moisture detection system and method which utilizes terahertz (THz) radiation to detect moisture on the surface of carbon fiber composite materials.

BACKGROUND

In the fabrication of aircraft and other structures using carbon fiber composite materials, it may be necessary to apply paint, other coatings, or adhesives to the surface of the composite material. However, during the application of paint, other coatings, or adhesives to the surface of a composite material the presence of moisture may compromise the strength of the adhesion between the coating and the material. Therefore, it may be necessary to characterize the moisture levels of composite material surfaces prior to application of coatings or adhesives to the surfaces.

Conventional methods of measuring moisture on surfaces of composite materials include cutting and weighing samples of the material to infer water content on like-sized parts or coupons of the material. Other methods may include heating the samples and measuring the quantity of moisture which is evaporated from the samples. Infrared and microwave electromagnetic radiation can be used to interact with moisture. The terahertz regime at higher frequency offers particular sensitivity.

Many non-conducting, dry materials that are opaque to infrared and visible light exhibit low absorption in the terahertz (THz) frequency range. The terahertz frequency range is commonly described as $1 \times 10^{11}$ to $1 \times 10^{13}$ Hz (1 to 0.01 mm wavelength). Absorption of radiation in the THz frequency range increases with the quantity of moisture on the surface of a material.

Accordingly, a moisture detection system and method are needed which utilize absorption of radiation in the THz frequency range by moisture to facilitate stand-off, non-contact and non-destructive characterization of moisture levels on composite materials.

The features, functions, and advantages that have been discussed can be achieved independently in various embodiments of the present disclosure or may be combined in yet other embodiments further details of which can be seen with reference to the following description and drawings

SUMMARY

Brief Description of the Illustrations

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
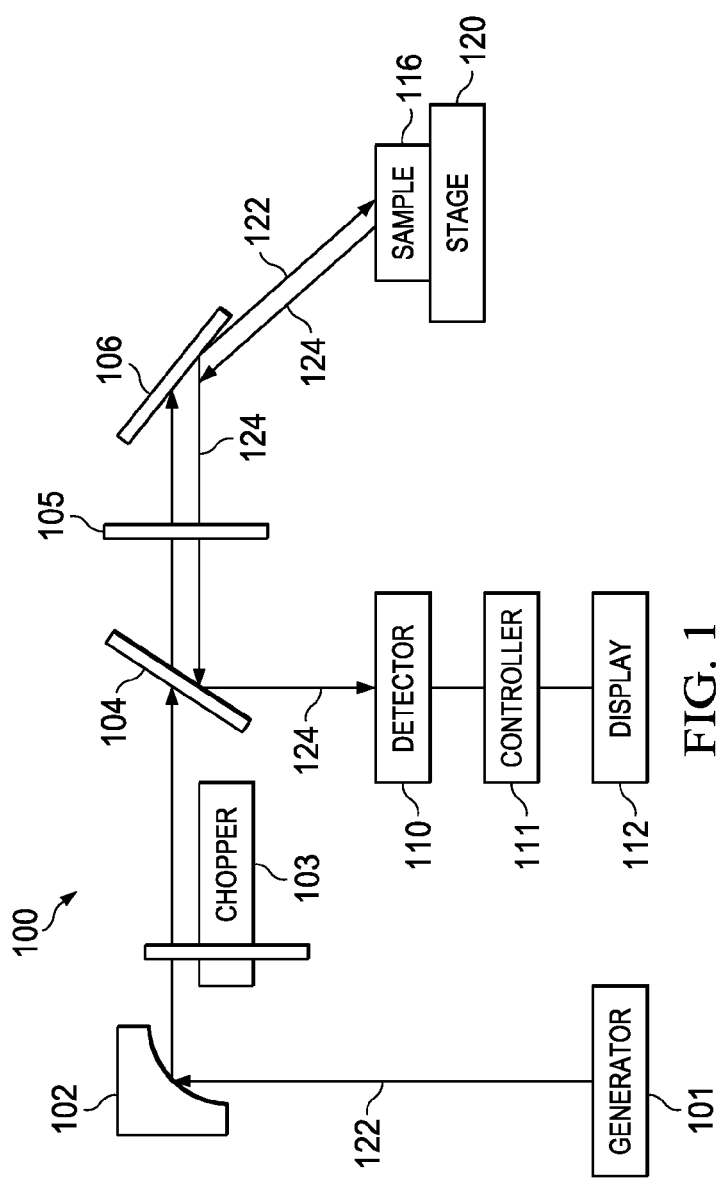
FIG. 1 is a schematic diagram of an illustrative embodiment of a moisture detection system which is suitable for implementation of the moisture detection method.

Referring initially to FIG. 1, an illustrative embodiment of the moisture detection system, hereinafter system, is generally indicated by reference numeral 100. The system 100 may include a generator 101. The generator 101 may be adapted to generate an incident beam 122 having a radiation in the terahertz range of from about $1 \times 10^{12}$ Hz (or 100 GHz) to about $1.5 \times 10^{12}$ Hz (or 1.5 THz). In some embodiments, the generator 101 may be a Gunn diode oscillator with an output power of 12 mW.

A parabolic mirror 102 may be positioned in beam-receiving relationship with respect to the output of the generator 101. The parabolic mirror 102 may be adapted to focus the incident beam 122. A beam splitter 104 may be positioned in beam-receiving relationship with respect to the parabolic mirror 102. An optical chopper 103 may be disposed between the parabolic mirror 102 and the beam splitter 104. A polyethylene Fresnel lens 105 may be positioned at a first beam-receiving location with respect to the beam splitter 104. In some embodiments, the Fresnel lens 105 may have a thickness of about 5 mm. A mirror 106 may be spaced-apart with respect to the Fresnel lens 105. A stage 120 may be disposed at a selected position with respect to the mirror 106. The stage 120 may be adapted to support a sample 116 the surface moisture content of which is to be measured using the system 100. The stage 120 may be a turntable and may additionally be adapted to selectively move the sample 116 along X, Y and Z axes according to the knowledge of those skilled in the art.

A detector 110 may be positioned at a second beam-receiving location with respect to the beam splitter 104. A controller 111 may interface with the detector 110. A display 112 may interface with the controller 111.

In exemplary application of the system 100, a sample 116 is placed on the stage 120. The sample 116 has or is suspected to have moisture contamination on the surface of the sample 116. The generator 101 emits an incident beam 122 which may have a wavelength in the terahertz range (from about 100 GHz to about 1.5 THz) against the parabolic mirror 102. The parabolic mirror 102 focuses the incident beam 122 to a selected size (such as 4 mm, for example and without limitation) and the optical chopper 103 modulates the incident beam 122 to a selected frequency (such as 1.2 kHz, for example and without limitation). The focused and modulated incident beam 122 is transmitted through the Fresnel lens 105, which focuses the incident beam 122 to a selected focal length (such as 204 mm, for example and without limitation). In some applications, the distance between the focus of the parabolic mirror 102 and the focus of the Fresnel lens 105 may be about 408 mm.

Figure 2:
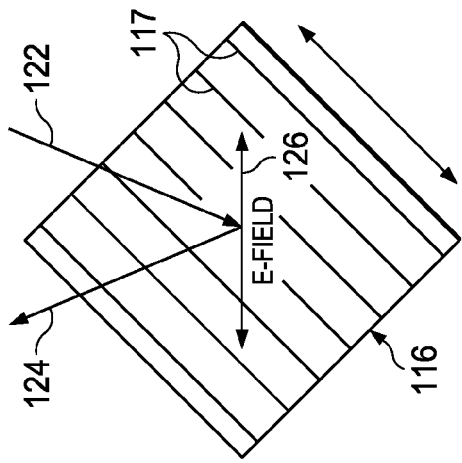
FIG. 2 is a schematic diagram which illustrates application of a focused beam of radiation in the terahertz range to the surface of a composite material at an angle of approximately 45 degrees with respect to the primary direction of the carbon fibers in the composite material.

The incident beam 122 which is transmitted through and focused by the Fresnel lens 105 strikes the mirror 106, which deflects the incident beam 122 toward and then against the surface of the sample 116. As shown in FIG. 2, the stage 120 (FIG. 1) may be positioned in such a manner that the electric field 126 of the incident beam 122 is oriented at an angle of approximately 45 degrees with respect to the carbon fiber direction 117 of the carbon fiber composite material sample 116. Any moisture which may be present on the surface of the sample 116 absorbs energy from the incident beam 122. The amount of energy which the moisture absorbs from the incident beam 122 varies with the amount of moisture on the surface of the sample 116.

A reflected beam 124 is reflected from the surface of the sample 116 to the mirror 106. The mirror 106 deflects the reflected beam 124 through the Fresnel lens 105 and to the beam splitter 104, respectively. The beam splitter 104 deflects the reflected beam 124 to the detector 110. The detector 110 measures the amount of reflected energy in the reflected beam 124 and transmits the measurement data to the controller 111. The controller 111 correlates the amount of reflected energy in the reflected beam 124 with the quantity of moisture on the surface of the sample 116. The display 112 may present the quantity of moisture on the surface of the sample 116 in a percentage, graphical or other format. Prior to analysis of the moisture content on the surface of the sample 116, calibration of the system 100 may be accomplished by correlating degrees of moisture on the surfaces of standards with the amount of radiation reflected from the surfaces of the standards.

In some embodiments, after initial analysis of the reflected beam 124, incident beams 122 of various frequencies within the THz frequency range may be transmitted against the surface of the sample 116 to obtain a spectrum of frequencies of the reflected beams 124. The incident beams 122 may have frequencies in the range of 0.1 to 1.5 THz. The spectral reflection terahertz analysis may provide for distinct calibration of power as a function of frequency for the incident beams 122.

Figure 3:
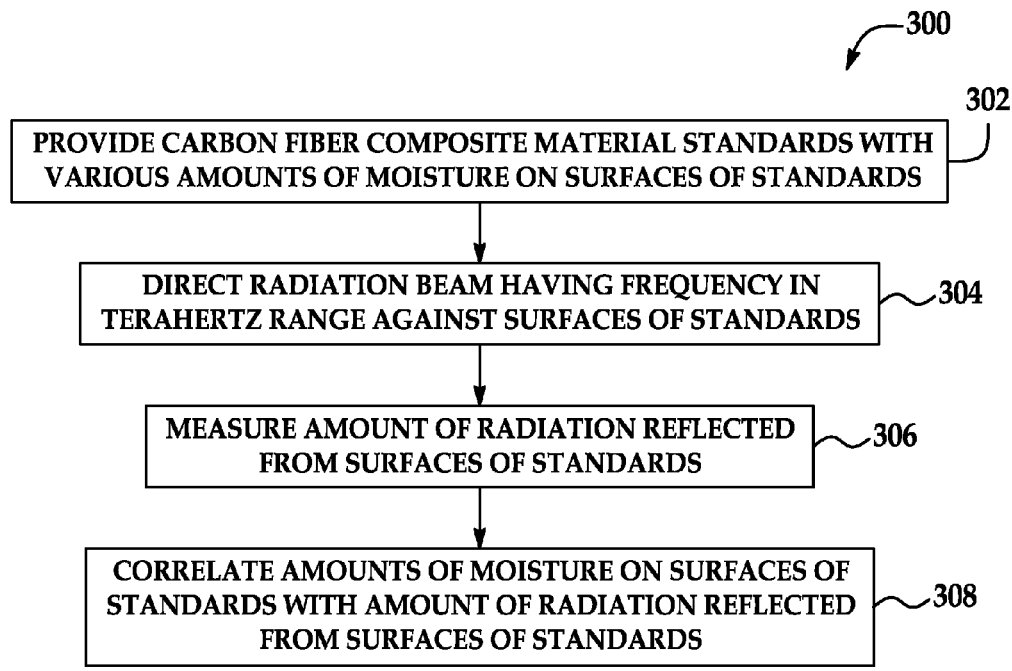
FIG. 3 is a flow diagram which illustrates calibration of a moisture detection system according to an illustrative embodiment of the moisture detection method.

Referring next to FIG. 3, a flow diagram 300 which illustrates calibration of a moisture detection system according to an illustrative embodiment of the moisture detection method is shown. In block 302, carbon fiber composite material standards with various amounts of moisture on the surfaces of the respective standards may be provided. In block 304, an incident radiation beam having a frequency in the terahertz range may be directed against the surfaces of the standards, respectively. In block 306, the amount of radiation which is reflected from the surfaces of the standards may be measured. In block 308, the amounts of moisture on the surfaces of the respective standards may be correlated with the amount of radiation which is reflected from the surfaces of the standards.

Figure 3A:
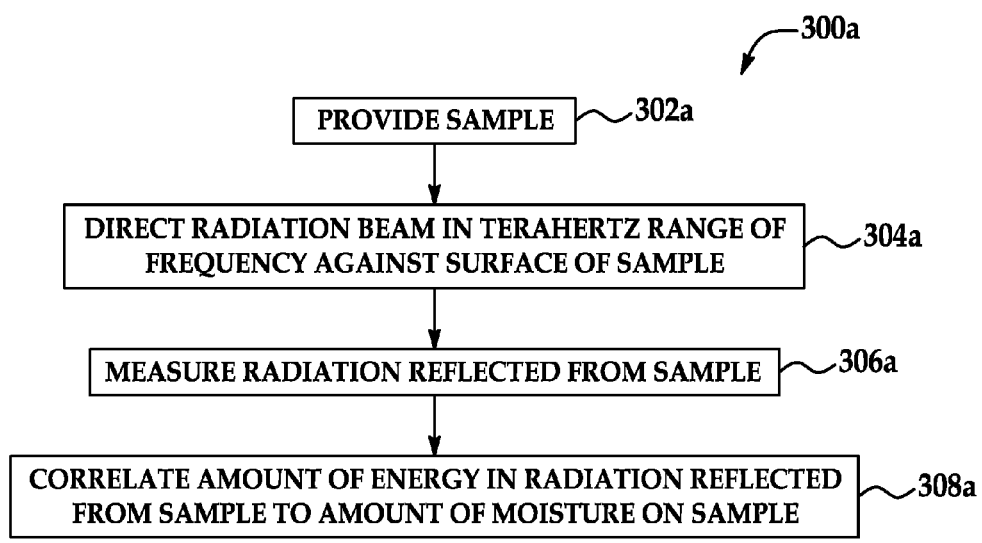
FIG. 3A is a flow diagram which illustrates characterization of moisture on the surface of a sample using a single THz frequency in implementation of an illustrative embodiment of the moisture detection method.

Referring next to FIG. 3A, a flow diagram 300a which illustrates characterization of moisture on the surface of a sample using a single THz frequency in implementation of an illustrative embodiment of the moisture detection method is shown. In block 302a, a sample is provided. In some embodiments, the sample may be carbon fiber composite material sample. In block 304a, a radiation beam having a frequency in the tetrahertz range is directed against a surface of the sample. In some embodiments, a radiation beam may be directed against the surface of the sample at about a 45-degree angle with respect to a primary direction of carbon fibers in the sample. In some embodiments, a radiation beam in the terahertz range of about 100 GHz to 1.5 THz may be directed against the surface of the sample. In block 306a, the amount of radiation reflected from the surface of the sample is measured. In block 308a, the amount of energy in the radiation reflected from the sample is correlated to the amount of moisture on the surface of the sample. In some embodiments, the method may include directing radiation beams in the terahertz range of about 0.1 to about 0.5 THz against the surface of the sample, measuring radiation from the radiation beams reflected from the sample and correlating amounts of energy in the radiation beams reflected from the sample to amounts of moisture on the sample.

Figure 4:
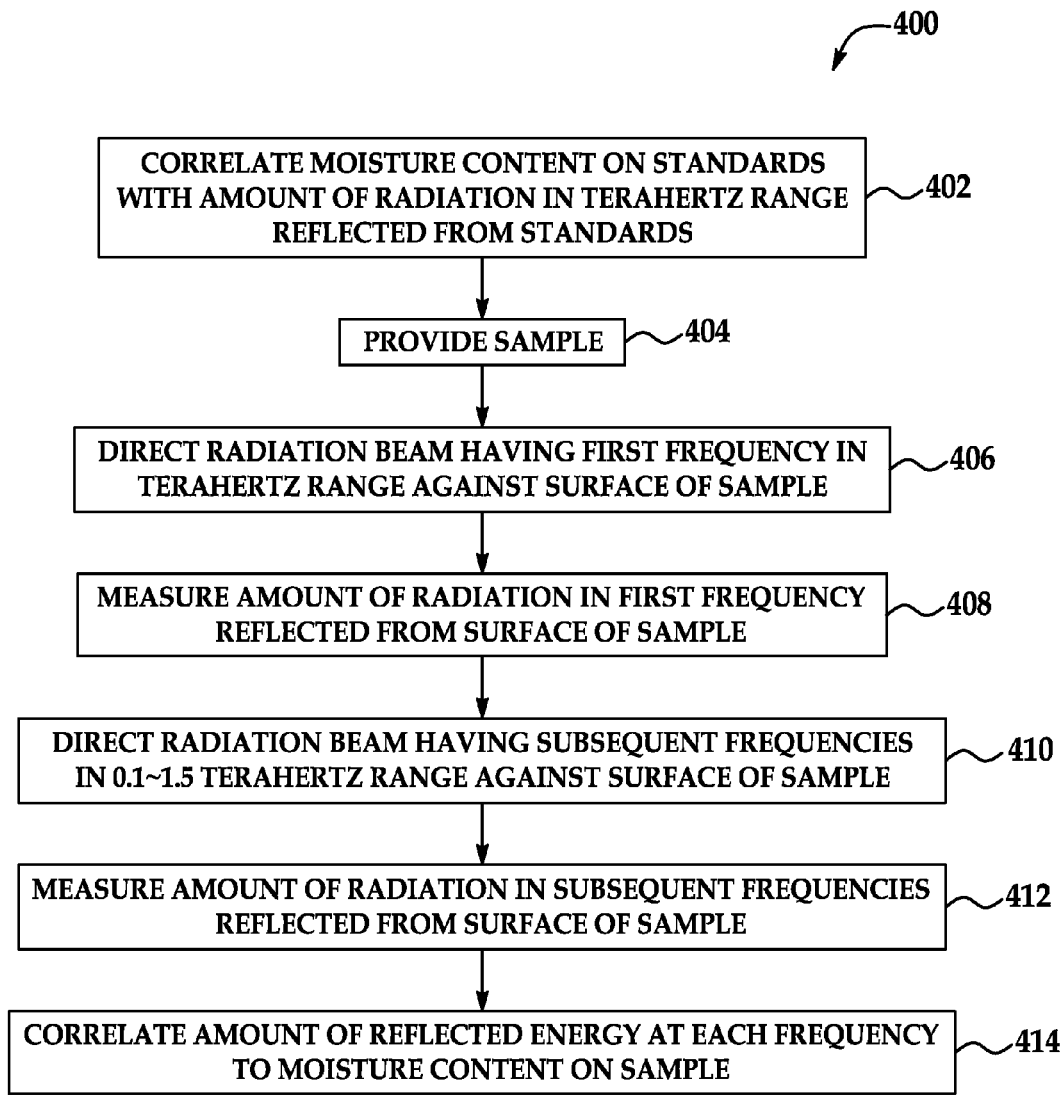
FIG. 4 is a flow diagram which illustrates characterization of moisture on the surface of a sample in implementation of an illustrative embodiment of the moisture detection method.

Referring next to FIG. 4, a flow diagram 400 which illustrates characterization of moisture on the surface of a sample such as a composite material, for example and without limitation, in implementation of an illustrative embodiment of the moisture detection method is shown. In block 402, various amounts of moisture on different standards may be correlated with the amounts of radiation in the terahertz range which is reflected from the respective standards. In block 404, a sample with an unknown level of moisture on its surface may be provided. In some embodiments, the sample may be a carbon fiber composite material. In block 406, a radiation beam having a first frequency in the terahertz range may be directed against the surface of the sample. In embodiments in which the sample is a composite material, the radiation beam may be directed against the composite material at 45 degrees relative to the primary direction of carbon fibers in the material. In some applications, the radiation beam may have a frequency in the range of 100 GHz to 1.5 THz. In block 408, the amount of radiation in the first frequency reflected from the surface of the sample in block 406 may be measured. In block 410, a radiation beam having subsequent frequencies in the terahertz range of 0.1 to 1.5 THz may be directed against the surface of the sample. In embodiments in which the sample is a composite material, the radiation beam may be directed against the material at 45 degrees relative to the primary direction of carbon fibers in the material. In block 412, the amount of radiation in the subsequent frequencies which were reflected from the surface of the sample in block 410 may be measured. In block 414, the amount of energy which was reflected from the sample at each frequency may be correlated with the amount of moisture on the surface of the sample.

Figure 5:
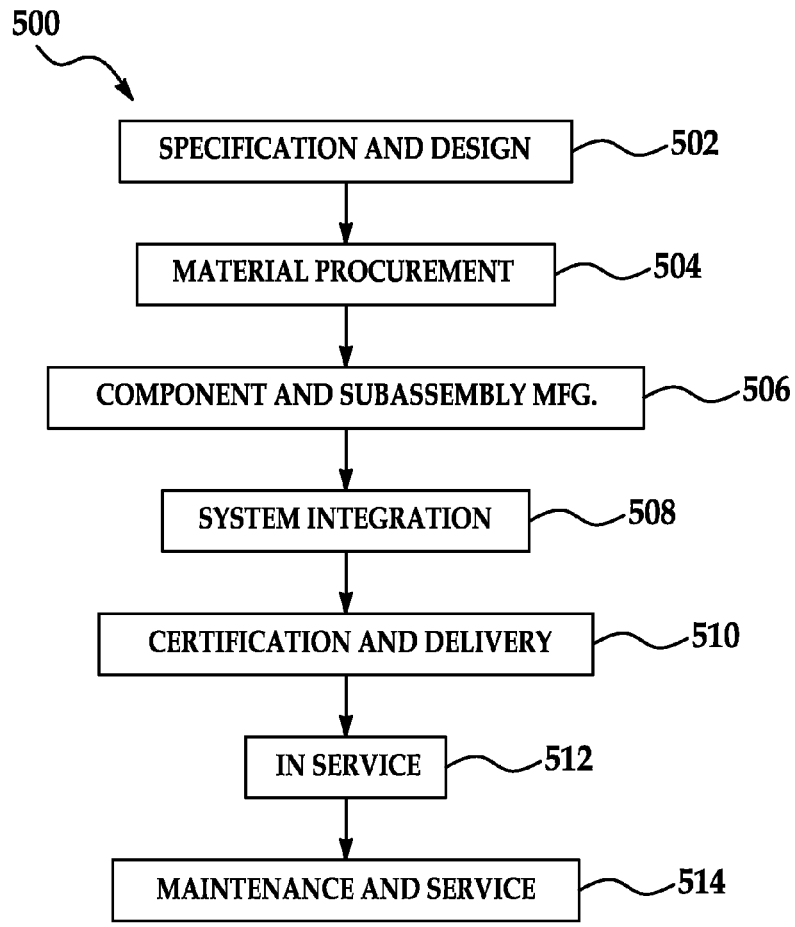
FIG. 5 is a flow diagram of an aircraft production and service methodology.
Figure 6:
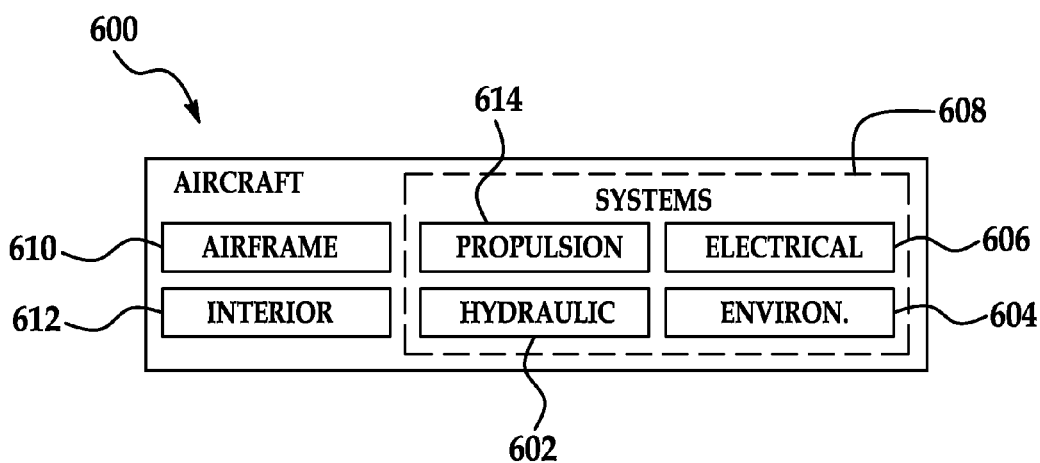
FIG. 6 is a block diagram of an aircraft.

Referring next to FIGS. 5 and 6, embodiments of the disclosure may be used in the context of an aircraft manufacturing and service method 500 as shown in FIG. 5 and an aircraft 600 as shown in FIG. 6. During pre-production, exemplary method 500 may include specification and design 502 of the aircraft 600 and material procurement 504. During production, component and subassembly manufacturing 506 and system integration 508 of the aircraft 600 takes place. Thereafter, the aircraft 600 may go through certification and delivery 510 in order to be placed in service 512. While in service by a customer, the aircraft 600 may be scheduled for routine maintenance and service 514 (which may also include modification, reconfiguration, refurbishment, and so on).

Each of the processes of method 500 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 600 produced by exemplary method 500 may include an airframe 610 with a plurality of systems 608 and an interior 612. Examples of high-level systems 608 include one or more of a propulsion system 614, an electrical system 606, a hydraulic system 602, and an environmental system 604. Any number of other systems may be included. Although an aerospace example is shown, the principles of the invention may be applied to other industries, such as the automotive industry.

The apparatus embodied herein may be employed during any one or more of the stages of the production and service method 500. For example, components or subassemblies corresponding to production process 506 may be fabricated or manufactured in a manner similar to components or subassemblies produced while the aircraft 600 is in service. Also one or more apparatus embodiments may be utilized during the production stages 506 and 508, for example, by substantially expediting assembly of or reducing the cost of an aircraft 600. Similarly, one or more apparatus embodiments may be utilized while the aircraft 600 is in service, for example and without limitation, to maintenance and service 514.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A moisture detection system for characterizing surface moisture content of a sample, comprising:
    a generator adapted to emit an incident beam of radiation from a terahertz spectrum of frequency onto the sample, wherein the sample comprises a carbon fiber composite material and wherein a direction of an electric field of the incident beam in a plane of a surface of the sample is oriented at an angle of about 45 degrees with respect to a carbon fiber direction in the plane of the surface of the sample;
    a detector adapted to receive a reflected beam of radiation from the sample and measure radiation in the reflected beam; and
    a controller adapted to correlate the radiation in the reflected beam with an amount of moisture.

2. The system of claim 1 further comprising a stage adapted to support the sample.

3. The system of claim 2 wherein the stage comprises a turntable.

4. The system of claim 2 wherein the stage is movable along X, Y and Z axes.

5. The system of claim 1 wherein the generator is adapted to emit an incident beam of radiation having a terahertz frequency of about 100 GHz to 1.5 THz onto the sample.

6. The system of claim 1 further comprising a display interfacing with the controller.

7. The system of claim 1 further comprising an optic chopper positioned to receive the incident beam from the generator.

8. The system of claim 7 further comprising a Fresnel lens positioned to receive the incident beam from the optic chopper.

9. The system of claim 1 wherein the generator comprises a Gunn diode oscillator.

10. The system of claim 1 wherein the detector comprises a Schottky diode.

11. The system of claim 1 further comprising a parabolic mirror positioned in beam-receiving relationship to the generator and a mirror positioned in beam-receiving relationship to the parabolic mirror.

12. A method of characterizing surface moisture content of a sample, comprising:
    providing a sample, wherein the sample comprises a carbon fiber composite material;
    directing a radiation beam in a terahertz range of frequency against a surface of the sample, wherein a direction of an electric field of the radiation beam in a plane of the surface of the sample is oriented at an angle of about 45 degrees with respect to a carbon fiber direction in the plane of the surface of the sample;
    measuring radiation reflected from the sample; and
    correlating an amount of energy in the radiation reflected from the sample to an amount of moisture.

13. The method of claim 12 wherein directing a radiation beam in the terahertz range of frequency against a surface of the sample comprises directing a radiation beam in the terahertz range of about 100 GHz to 1.5 THz against a surface of the sample.

14. The method of claim 12 further comprising directing radiation beams in the terahertz range of about 0.1 to about 0.5 THz against the surface of the sample.

15. A method of characterizing surface moisture content of a sample, comprising:
    correlating moisture content on a plurality of standards with an amount of radiation in a terahertz range reflected from the standards, respectively;
    providing a sample, wherein the sample comprises a carbon fiber composite material;
    directing a radiation beam having a first frequency in a terahertz range of frequency against a surface of the sample, wherein a direction of an electric field of the radiation beam in a plane of the surface of the sample is oriented at an angle of about 45 degrees with respect to a carbon fiber direction in the plane of the surface of the sample;
    measuring radiation in the radiation beam having a first frequency reflected from the sample;
    directing radiation beams having subsequent frequencies in the terahertz range of frequency against the surface of the sample, wherein directions of electric fields of the radiation beams having subsequent frequencies in the plane of the surface of the sample are oriented at an angle of about 45 degrees with respect to the carbon fiber direction in the plane of the surface of the sample;
    measuring radiation in the radiation beams having subsequent frequencies reflected from the sample; and
    correlating amounts of reflected energy in the radiation beam having a first frequency reflected from the sample and the radiation beams having subsequent frequencies reflected from the sample to amounts of moisture.

16. The method of claim 15 wherein directing radiation beams having subsequent frequencies in the terahertz range of frequency against the surface of the sample comprises directing radiation beams having frequencies of about 0.1 to 1.5 THz.

* * * * *